(12) United States Patent
Müller

(10) Patent No.: US 10,555,869 B2
(45) Date of Patent: Feb. 11, 2020

(54) SYSTEM FOR ASSISTING A HELPER IN THE RESUSCITATION OF A PERSON WITH CIRCULATORY ARREST

(71) Applicants: Michael Müller, Bühl (DE); Matthias Roth, Freiburg (DE); Per Schorling, Svendborg (DK)

(72) Inventor: Michael Müller, Bühl (DE)

(73) Assignees: Michael Müller, Bühl (DE); Matthias Roth, Freiburg (DE); Per Schorling, Svendborg (DK)

( * ) Notice: Subject to any disclaimer, the term of this patent is extended or adjusted under 35 U.S.C. 154(b) by 343 days.

(21) Appl. No.: 15/124,706

(22) PCT Filed: Jan. 13, 2015

(86) PCT No.: PCT/DE2015/100017
§ 371 (c)(1),
(2) Date: Sep. 9, 2016

(87) PCT Pub. No.: WO2015/110118
PCT Pub. Date: Jul. 30, 2015

(65) Prior Publication Data
US 2017/0046494 A1     Feb. 16, 2017

(30) Foreign Application Priority Data

Jan. 22, 2014 (DE) .......... 10 2014 100 710
Feb. 27, 2014 (DE) .......... 10 2014 102 590

(51) Int. Cl.
*G09B 23/28* (2006.01)
*A61H 31/00* (2006.01)
*G09B 5/02* (2006.01)

(52) U.S. Cl.
CPC ......... *A61H 31/005* (2013.01); *A61H 31/007* (2013.01); *G09B 5/02* (2013.01);
(Continued)

(58) Field of Classification Search
CPC .. G09B 23/288; A61H 31/005; A61H 31/007; G06F 19/3481
See application file for complete search history.

(56) References Cited

U.S. PATENT DOCUMENTS 6,272,075 B1 * 8/2001 Paganelli ............. G04G 9/0064
368/10
6,440,082 B1 * 8/2002 Joo ....................... A61B 5/0535
600/483

(Continued)

*Primary Examiner* — Peter R Egloff
(74) *Attorney, Agent, or Firm* — Michael Soderman

(57) ABSTRACT

The invention relates to a system for assisting a helper (8) in the performance of chest compressions for the immediate resuscitation of a person (1) affected by a circulatory arrest, wherein the helper (8) may be an untrained novice helper, in particular. In order to identify the circulatory condition of the person (1) and impart assistive first measures, a position sensor (4) connected to a support of similar design to a sticking plaster (5) is arranged on the sternum (2) of the person (1) by means of adhesion at an appropriate position. The position sensor (4), which is in the form of an acceleration sensor, is additionally connected to a mobile terminal (6) wirelessly or by wire. This terminal (6) is in the form of a smartphone, the smartphone being equipped with an appropriate application program (7).

7 Claims, 1 Drawing Sheet

(52) U.S. Cl.
CPC .... *G09B 23/288* (2013.01); *A61H 2201/5043* (2013.01); *A61H 2201/5064* (2013.01)

(56) References Cited

U.S. PATENT DOCUMENTS

| | | | | |
|---|---|---|---|---|
| 2006/0223042 | A1* | 10/2006 | Epler | G09B 7/00 |
| | | | | 434/323 |
| 2006/0270952 | A1 | 11/2006 | Freeman et al. | |
| 2008/0171311 | A1 | 7/2008 | Centen et al. | |
| 2008/0312565 | A1 | 12/2008 | Celik-Butler et al. | |
| 2010/0022904 | A1 | 1/2010 | Centen | |
| 2010/0256539 | A1* | 10/2010 | Strand | A61H 31/005 |
| | | | | 601/41 |
| 2011/0112593 | A1* | 5/2011 | Freeman | A61H 31/005 |
| | | | | 607/6 |
| 2011/0117878 | A1* | 5/2011 | Barash | H04W 4/90 |
| | | | | 455/404.2 |
| 2012/0184882 | A1* | 7/2012 | Totman | A61B 5/1135 |
| | | | | 601/41 |
| 2013/0296719 | A1* | 11/2013 | Packer | A61B 5/0205 |
| | | | | 600/484 |
| 2014/0043149 | A1* | 2/2014 | Cowan | A61N 1/3993 |
| | | | | 340/12.5 |
| 2014/0342331 | A1* | 11/2014 | Freeman | G09B 23/288 |
| | | | | 434/265 |

\* cited by examiner

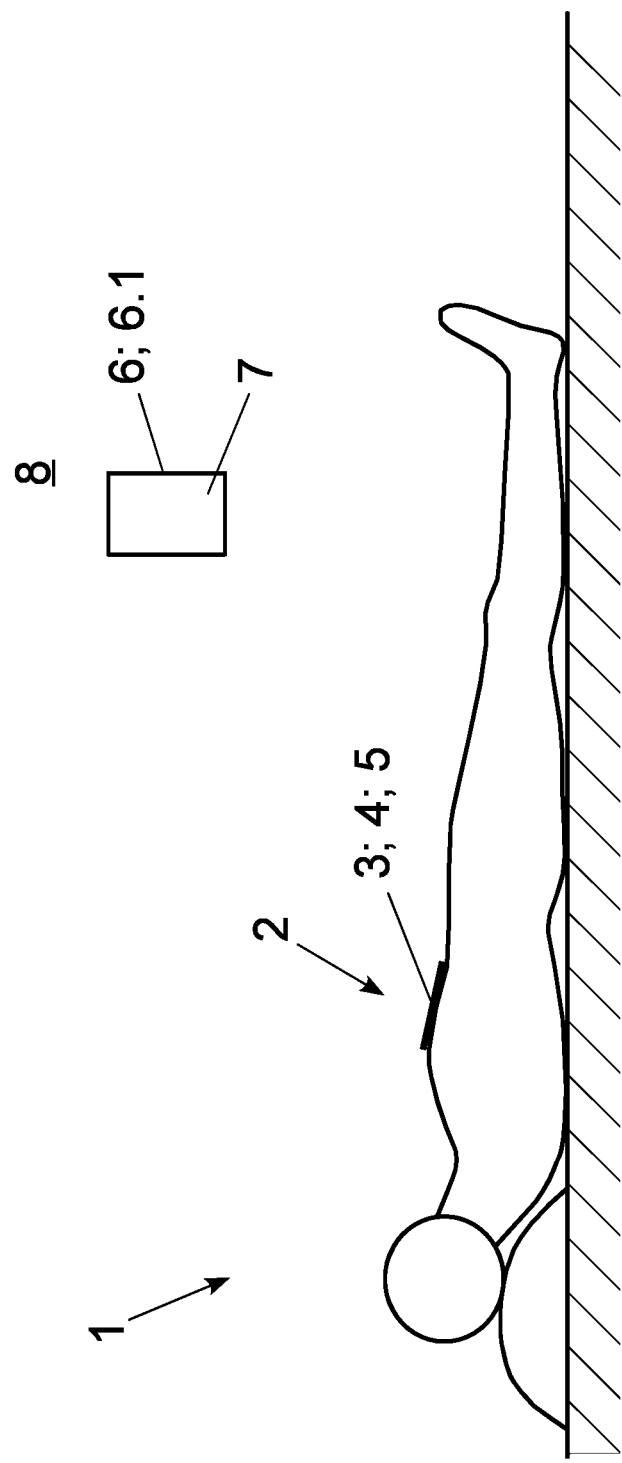

SYSTEM FOR ASSISTING A HELPER IN THE RESUSCITATION OF A PERSON WITH CIRCULATORY ARREST

CROSS REFERENCE TO RELATED APPLICATIONS

This application is the U.S. national stage of International Application No. PCT/DE2015/100017, filed on 2015 Jan. 13. The international application claims the priority of DE 102014100710.7 filed on 2014 Jan. 22 and the priority of DE 102014102590.3 filed on 2014 Feb. 27; all applications are incorporated by reference herein in their entirety.

BACKGROUND

The invention relates to a system for assisting a helper in the performance of first aid measures for the immediate resuscitation of a person and a patient, respectively, affected by a circulatory arrest.

Sudden cardiac death is a leading cause of death. Despite considerable efforts in recent decades and the establishment of international guidelines for the treatment of cardiovascular arrest the survival rate stays below 10%. Most of the 75,000 people suffering from a cardiac arrest every year in Germany die or survive with permanent neurological damage and, therefore, require permanent care. The main problems in the fight against sudden cardiac death are the following:

Survival after sudden cardiac death is only possible if chest compressions are started before the arrival of the emergency services within the first few minutes, while these need to be performed with adequate quality. This massage should be performed in accordance with the currently valid recommendations given by the guidelines. At present, the recommendation is a compression depth of 5-6 cm and a frequency of for example 100/min as well as a complete relief after each chest compression. The interruptions of chest compressions—for example in order to ventilate or trigger a defibrillation shock—should be as short as possible so that the brain continuously is supplied with blood and no irreversible damage occurs.

In Germany only about 20% of the lay rescuers initiate the important measures of resuscitation (particularly chest compressions), whereas in other European countries this percentage reaches up to 70%. The quality of chest compressions after training on the basics is good, but deteriorates after six months again considerably. Furthermore, the quality of chest compressions during performing CPR deteriorates considerably already after two minutes.

The probability of survival of a patient with cardiac arrest depends essentially on the actions performed by the lay helper, who, however, is often overwhelmed by the situation and lacks appropriate training.

According to the internal state of the art a method for defibrillation while performing chest compression by a helper as well as a defibrillator used therefor is known, wherein the number of chest compressions performed is determined and after a specified number of compressions after initiation of the measures or after a defibrillator shock, another defibrillator shock is delivered, whereas the chest compressions can be continued during the delivery of the defibrillator shock.

Furthermore, from the internal state of the art a defibrillator system is known having a control unit to control the defibrillator and to display data relevant for resuscitation. Herein, bidirectional data goggles are used as the control unit, which allow controlling the control unit by movement of the eyes (eye tracking).

In addition, an ultrasound system and a method for communication between an ultrasonic device and bidirectional data goggles are known, wherein the data goggles depict an ultrasound image on a transparent display, whereas simultaneously the data goggles permit the user to look at the surgical site on the patient. The display also includes a device for tracking the eye movement (eye tracking), whereby the data goggles are designed as a control unit for the ultrasonic device. By connecting the data goggles to a surveillance monitor important values, which are denoted vital parameters, about the condition of the patient are transferred to the data goggles.

EP 1 128 795 B1 discloses a system for measuring and causing breast-compressions. It includes a mobile CPR compression monitor (CPR—cardiopulmonary resuscitation) for monitoring the chest compressions during resuscitation of a person affected by a cardiac arrest. The device is placed on the hand of the helper or the patient and comprises acceleration sensors and an interface for data transmission. An evaluation unit with monitor is connected to this interface via a cable. This evaluation unit with monitor can be integrated in the CPR compression monitor or be a stand-alone device. This system is designed for trained and experienced medical staff.

WO 2011/156374 A3 discloses a wireless ultrasound health condition monitoring system. The system, comprising a sensor unit with converter logic and sound transmitter, reads physiological signals and transmits them by means of sound/ultrasound to a receiving device (phone or computer). The sensor unit, comprising a plurality of electrodes, is arranged on a protective case for a smart phone. By use of the electrodes contacting the patient's skin an ECG (ECG—electrocardiogram recording of the heart rhythm) is recorded and transmitted to a receiver, for example a smartphone inserted into the protective case, using sound.

U.S. Pat. No. 8,509,882 B2 describes a software application (app) for a smartphone that can display and evaluate ECG signals transmitted by sound. In addition, voices, GPS data or movements of the smartphone can be recorded. The collected data can be transferred to a web server.

WO 2006/104977 A2, EP 2 255 845 A1 and DE 60 2004 002 147 T2 disclose a professional medical system to support a first aider, who must be trained in resuscitation. The system includes, among other things, a defibrillator and a mobile display and control unit.

Similarly, EP 1 858 472 B1 describes a mobile, but complex medical system for assisting a helper during resuscitation, which also includes a defibrillator. It is intended to deploy the device at a few central locations with high numbers of people congregating, so first aiders can get a quick access to it. However, this device too can be used reasonably only by trained helpers.

Likewise, US 2008/171311 A1 discloses a professional medical device, which may be used for CPR. Said device comprises an assist device, which is to be fixed e.g. at the wrist of the helper, and a basis unit communicating with the assist device.

US 2008/312565 A1 describes a standalone device for assisting a helper during resuscitation, comprising a sensor, a processing unit, batteries, a display and a radio module. This device is to be placed on the sternum of the patient. However, size and rigidity of said device hamper performing chest compressions.

Methods and apparatuses for accurately determining the depth of compressions during chest compressions are shown in WO 2004/037 154 A2, US 2010/022904 A1 and DE 11 2010 000 978 T5.

Significant disadvantages of the known prior art solutions are that an application of appropriate help measures is time consuming and the respective (first) helper often is overburdened and insufficiently trained. In addition, a high level of knowledge is required to be capable of carrying out a successful emergency treatment of the patient.

Especially for systems with automatic defibrillator it could be shown that until beginning of the first chest compressions a comparatively long period of time—on average almost two minutes—is lost due to preparatory actions (see e.g.: M P Müller et al., "An AED Is Not An AED", presented at the American Heart Assoc. ReSS 2014, Nov. 7 to 10, 2014 in Chicago, USA). In particular, at the beginning of the emergency treatment electrodes must first be fixed, the automatic defibrillator must be started and (automated) measurements and analyzes be carried out, during which time no lifesaving chest compressions are performed. However, this is in stark contrast to the recommendations for resuscitation, according to which as soon as possible, i. e. after less than 30 seconds, chest compressions are to be initiated.

SUMMARY

The objective of the present invention is to provide a solution that enables an untrained lay rescuer to immediately perform guided first lifesaving measures in order to help a person affected by circulatory arrest, in the following called patient, and professionally assists by supplying essential information about type of measures to be carried out and success of these measures for resuscitation, the aim being to avoid irreversible damage to the patient due to cardiac arrest before arrival of medical trained helpers.

The objective is achieved according to the invention with the features according to the patent claim 1; advantageous implementations of the invention are described in the dependent claims 2 to 6. Claim 7 discloses a beneficial use of the invention.

DETAILED DESCRIPTION

According to the invention, a system for guidance and support (also referred to as "support system") of a helper, who especially is an untrained lay in resuscitation, during resuscitation of patients with cardiac arrest is provided. The support system includes a mobile terminal device, a software application (i.e., a computer-executable program) for this terminal device, and a position sensor affixed to a support means.

The mobile terminal device is configured such that standalone software applications are executable on the terminal device. Preferably, this mobile terminal device is an electronic device typically taken along by people in their everyday life. The mobile terminal device may be any type of portable small or microcomputer, such as a smartphone, a phablet, tablet, or netbook.

The mobile terminal device is by use of a software application executable on the device, for example in the form of a so-called app, designed such that it assists the helper in the necessary resuscitation measures—particularly the recognition of the circulatory condition of the patient, making an emergency call and performing physical aid measures—, so it is particularly suited to support inexperienced lay helpers.

The mobile terminal device is preferably a smartphone, that is a small computer with telephony function; accordingly, the software application is a smartphone app.

The mobile terminal device can be configured by the software application that in a first step, a query of symptoms (of the patient to be treated) is carried out, where it is determined by the terminal device, based on the results of the query, whether the patient actually sustained a circulatory arrest or not. In this first step very simple and even for a beginner understandable queries of the symptoms may be made by the software application in order to determine whether or not a cardiac arrest occurred.

Furthermore, the mobile terminal device and the software application may be configured such that an emergency call is placed automatically, e. g. to the appropriate PSAP (PSAP—public-safety answering point). The emergency call can e. g. be sent in the form of an audio message or a text message. The mobile terminal device and the software application can be configured so that the emergency call is made as a function of the result of the symptom query (where an emergency call is only then issued when the symptom query has revealed that a cardiac arrest actually occurred). However, it can also be provided that the emergency call is issued independently of the result of the symptom query, so that the emergency call is not delayed by the period of time required for the symptom query. In the latter case, for example, it may be provided to automatically place the emergency call simultaneously with the symptom query activation, said emergency call just being triggered by activation of the symptom query.

Advantageously, the software application may access positioning data and location coordinates, respectively, via an interface in the operating system of the mobile terminal device. The mobile terminal device may comprise, for example, a receiver (e. g. GPS receiver) for a (e. g. satellite-based) navigation and positioning system (e. g. the Global Positioning System GPS), and be designed in such a manner that the current position of the terminal is determined by means of the receiver. The mobile terminal device may also be configured such that a determination of its location is possible by a triangulation of transmission masts (e.g. antennas designated for mobile telephony) communicating with the mobile terminal device. It can be provided that these position coordinates are transmitted, e.g., as a constituent of the emergency call. Thus, the position of the first aider can be transmitted to the appropriate PSAP by means of the emergency call without additional effort or intervention by the helper.

The terminal device can also be configured or programmed such that a guidance of the helper to resuscitate the patient is done visually e. g. by means of a visual display of the terminal device and/or acoustically via a loudspeaker device of the terminal device. The terminal device is preferably configured such that a resuscitation instruction is issued, if the symptom-query has revealed that a cardiac arrest actually occurred.

The terminal device in particular can be configured such that it provides visual and/or audible instructions for chest compression, ventilation and optionally defibrillation, whereby a stand-alone defibrillator is required for defibrillation.

The position sensor is connected to a support means and is intended for applying (e. g. sticking) on the patient's skin over the sternum.

The support means for the position sensor is preferably designed as a sticking plaster or provided with such an adhesive tape, so that the position sensor, if necessary, can be fixed to the patient in a straightforward manner by gluing.

The sticking plaster or support means, respectively, can be a self-adhesive, flexible strip of fabric material and/or plastic, in which the position sensor is incorporated or to which the position sensor is applied. Thus, herein the term "sticking plaster" denotes a strip of e. g. fabric material and/or plastic (commonly employed in medicine), which is on one side at least partially provided with an adhesive layer to be attached to a patient's skin.

By means of the support means the position sensor is fixed (e.g. sticked) to the skin of the patient at a position on the sternum and brought to a communication-connection or connected, respectively, to the terminal device. When conducting chest compressions the associated compression movements can thus be detected by the position sensor. The mobile terminal device can in particular be designed such that by means of the position sensor the compression depth (by which the sternum is pushed during the compressions) and/or the frequency of chest compressions are detected, then the instructions of the helper are provided on basis of these detected values.

The position sensor may, for example, be an acceleration sensor, wherein from the acceleration values detected by the sensor, both, the depth of penetration as well as the compression rate can be calculated.

The invention is applicable to a patient affected by a cardiac arrest, wherein the first aider, who in particular may be an inexperienced lay helper, is supported promptly and guided professionally in the resuscitation of the patient and the implementation of necessary measures, for example performing a heart massage. By the system according to the invention being simply constructed and applicable without any prior knowledge, increased success rates for such resuscitations are possible.

The position sensor connected to the sticking plaster—also denoted as "sticking plaster against sudden cardiac death"—may be produced cost-efficiently, so that large numbers of these sticking plasters may be obtainable and a wide availability, e. g. at crowded places, in first aid kits for vehicles or with relatives of people with an increased risk of suffering a sudden cardiac arrest, is made possible. The smartphone app can be provided for the most widely used smartphone operating systems (iOS, Android, Windows).

The smartphone app and the "sticking plaster against sudden cardiac death" may help lay helpers, in particular not yet trained lays, to reduce anxieties and may provide valuable help and instructions, respectively, during conduction of resuscitation measures. These measures are suitable to increase the number and quality of resuscitations performed by lays. This again will increase the amount of patients surviving without any disability.

According to one embodiment, the support system is configured such that the guidance of the helper is performed based on the values detected by means of the position sensor. For this purpose, the mobile terminal device exhibits a (wired or wireless) interface for transmitting the measured values from the position sensor to the terminal device.

The support system is further preferably configured in such a way, that it provides the helper permanently and in real-time with feedback on the quality of chest compressions and instructs to high-quality chest compressions. For this purpose, the terminal device may be configured in such a way, that it compares actual values of the depth of compression and/or the compression rate to pre-set target values and gives a corresponding correction instruction in case of a deviation of the actual values from the target values.

According to one embodiment, the support system is configured such that by means of establishing the communication link between the terminal device and the position sensor (e. g. by connecting the position sensor to the terminal), the previously described support routine is started (automatically). Accordingly, no additional action from the helper to start the support routine must be undertaken.

BRIEF DESCRIPTION OF THE DRAWINGS

The invention will now be described by way of example and a drawing in which the FIGURE is an illustration of an embodiment of the system.

DETAILED DESCRIPTION OF THE PREFERRED EMBODIMENTS

The position sensor 4 is affixed to the skin 3 of the lying patient 1, who is affected by a cardiac arrest, at a position on his sternum 2 by means of the sticking plaster 5 as a the support means.

The position sensor 4 in this example is an inductively working movement sensor and, according to the embodiment, is connected wirelessly via a Bluetooth interface 6.1 (not depicted) with a smartphone as the mobile terminal device 6.

The smartphone 6 is programmed by an application (smartphone app) 7 (not depicted in detail) as a programmed executable, which gathers the data collected by the position sensor 4, processes said data and delivers corresponding information to a helper (not depicted), who particularly may be a lay helper, in order to aid said helper in a proper way, for example by way of acoustic or visual signals or a text message or a video, in executing necessary measures to help said patient 1.

Thus, the helper receives support in all required measures, such as recognition of a circulatory arrest, issuing an emergency call, conducting simple help measures, by means of the smartphone app 7 installed on the smartphone 6. The app starts a very simple and even for a lay understandable query regarding the symptoms of the patient 1 to be treated, in order to determine whether or not a cardiac arrest occurred. From the app, an emergency call to the responsible Rescue Coordination Centre will automatically be issued; furthermore, by means of the position determination integrated in the smartphone 6 the location of said smartphone 6 will be determined and forwarded.

Now the lay helper is guided in conducting chest compressions. For this purpose, each chest compression is measured by means of the position sensor 4, which is glued to the skin 3 of the patient 1 on his sternum 2. The feedback system of the smartphone app 7 delivers permanently and in real time feedback concerning the quality of the chest compressions and thus instructs to perform high-quality heart massages. Special focus is set on the using ergonomics of the software. The feedback from the app 7 is designed such that it is readily understandable for the lay rescuer who is in an extremely stressful situation and the instructions to improve quality are easy to implement.

LIST OF REFERENCE NUMERALS

1 Patient
2 Sternum
3 Skin

4 Position sensor
5 Sticking plaster; support means
6 Smartphone; mobile terminal device
6.1 Interface
7 Executable program; Application (App)

The invention claimed is:

1. A system for assisting a helper in performing chest compressions for resuscitation of a patient affected by a cardiac arrest, comprising a position sensor (4) and a mobile terminal device (6), which is connected to said position sensor (4) via an interface (6.1), said system being configured for detecting a circulation condition of said patient (1), characterized in that
the system lacks a defibrillator,
the position sensor (4) is connected to a sticking plaster (5) as a support means, said sticking plaster (5) being a flexible strip of fabric material and/or plastic and having an adhesive layer, wherein the sticking plaster (5) with said position sensor (4) being fixable on the skin (3) over the sternum (2) of the patient (1) by use of said adhesive layer,
said position sensor (4) is an acceleration sensor,
the mobile terminal device (6) is a commercially available smartphone, which is configured such that standalone software applications are executable,
the system comprises a stand-alone software application (7), which is stored and executed on the smartphone;
the software application (7) and the mobile terminal device (6) are configured to automatically initiate an emergency call in the form of audio, video or text message to a rescue coordination center,
said software application (7) being configured for
a. establishing a communication link between the position sensor (4), the mobile terminal device (6) and the helper (8),
b. querying symptoms detectable by the helper (8),
c. evaluating said symptoms in terms of determination of the circulatory arrest,
d. instructing the helper (8) in conducting short term necessary measures for resuscitation of the patient (1) and
e. acquiring and analyzing data detected by the position sensor (4),
wherein said querying of symptoms and said instructing the helper (8) in carrying out short-term necessary measures are designed such that they can be understood by an untrained lay rescuer.

2. The system according to claim 1, characterized in that the position sensor (4) is an inductive acceleration sensor.

3. The system according to claim 1, characterized in that the mobile terminal device (6) is connected to the position sensor (4) via the interface (6.1) by wire or wirelessly.

4. The system according to claim 1, characterized in that the software application (7) is configured to determine the current location of the helper (8) by means of interfaces to the operating system and/or a location determining system of the mobile terminal device (6).

5. The system according to claim 1, characterized in that the software application (7) is configured for
determining a depth of compression of the sternum (2),
determining acceleration values of a compression frequency of the compressions,
comparing the determined depth of compression and acceleration values to pre-set target values, and/or
instructing the helper (8) to correct said depth of compression and acceleration values.

6. The system according to claim 1, characterized in that the system is configured for automatically triggering and sending the emergency call when the querying of symptoms is started, wherein said emergency call is triggered both in a dependent as well as in an independent fashion based on a result of said queried symptoms.

7. Method for assisting a helper in performing chest compressions for resuscitation of a patient affected by a cardiac arrest with an apparatus made up of
a position sensor (4), which is connected to a sticking plaster (5) as a support means, wherein said position sensor (4) is an acceleration sensor;
a mobile terminal device (6) in the form of a commercially available smartphone; and
a software application (7) as an application program executable on the smartphone for establishing a communication link between the position sensor (4) and the mobile terminal device (6),
said apparatus lacking a defibrillator, characterized in that said method supports and guides an untrained lay helper (8) when carrying out short-term measures necessary for resuscitation of a patient (1), who is affected by a cardiac arrest, and comprises the following steps:
querying symptoms recognizable by the lay helper (8),
evaluating said symptoms as to diagnose a cardiac arrest and
guiding the lay helper in performing chest compressions for resuscitation of said patient (1), wherein during said chest compressions the data collected by said position sensor (4) fixed with said sticking plaster (5) on the skin (3) of the patient (1) over the sternum (2) are analyzed by means of the software application (7) and the lay helper (8) by means of the software application (7) is provided with feedback in real-time on a compression depth and/or frequency of chest compressions.

* * * * *